United States Patent [19]

Schwan

[11] 4,140,682
[45] Feb. 20, 1979

[54] BIS[3-(2,4-DIOXOIMIDAZOLIDINYL)]DIAZENE

[75] Inventor: Thomas J. Schwan, Norwich, N.Y.

[73] Assignee: Morton-Norwich Products, Inc., Norwich, N.Y.

[21] Appl. No.: 869,229

[22] Filed: Jan. 13, 1978

[51] Int. Cl.$^2$ .................... A01N 9/22; C07C 107/00; C07C 107/04
[52] U.S. Cl. .................... 260/140; 424/226; 548/310
[58] Field of Search .................... 260/140; 424/226

[56] References Cited

U.S. PATENT DOCUMENTS

| 3,773,746 | 11/1973 | Jack et al. | 260/140 |
| 3,892,724 | 7/1975 | Kollmeyer et al. | 260/140 |

Primary Examiner—Floyd D. Higel
Attorney, Agent, or Firm—Anthony J. Franze

[57] ABSTRACT

The compound bis[3-(2,4-dioxoimidazolidinyl)]diazene possesses activity as an antifungal agent.

1 Claim, No Drawings

BIS[3-(2,4-DIOXOIMIDAZOLIDINYL)]DIAZENE

This invention relates to a chemical compound. In particular, it is concerned with the compound bis[3-(2,4-dioxoimidazolidinyl)]-diazene.

This compound is an antifungal agent. At concentrations of 80, 10, and 100 μg/ml in Sabouraud's dextrose broth, it inhibits the growth of *Candida albicans, Microsporum canis,* and *Aspergillus niger,* respectively. It is thus adapted to be combined in various forms such as elixirs, dusts, unguents, solutions, and suspensions to provide compositions inimical to fungal growth.

The preparation of this compound can be accomplished by reacting 3-amino-2,4-imidazolidinedione with bromine water.

In order that this invention may be readily available to and understood by those skilled in the art, the following example is appended:

Bis[3-(2,4-dioxoimidazolidinyl)]diazene

To a solution of 11.5 g (0.10 mole) of 3-amino-2,4-imidazolidinedione in 500 ml of water stirred at 5°–6° was added, over 20 min., bromine (10.3 ml, 32 g, 0.20 mole). The mixture was stirred at 5°–10° for 15 min. and the solid was filtered, washed with 100 ml water, air dried, and dried at 60° to give 6.10 g (54%) of the product, m.p. 215°–220° (dec).

An analytical sample, m.p. 238°–240° (dec), was obtained by drying the product at 100° in vacuo.

Anal. Calcd. for $C_6H_6N_6O_4$: C, 31.87; H, 2.67; N, 37.16. Found: C, 31.69; H, 2.64; N, 36.84.

What is claimed is:

1. Bis[3-(2,4-dioxoimidazolidinyl)]diazene.